(12) United States Patent
Bey et al.

(10) Patent No.: US 11,884,611 B2
(45) Date of Patent: Jan. 30, 2024

(54) REACTOR FOR CARRYING OUT A GAS-LIQUID TWO-PHASE HIGH-PRESSURE REACTION WITH A FOAMING MEDIUM

(71) Applicant: BASF SE, Ludwigshafen am Rhein (DE)

(72) Inventors: Oliver Bey, Ludwigshafen am Rhein (DE); Peter Zehner, Weisenheim am Berg (DE); Michael Acker, Ludwigshafen am Rhein (DE); Rocco Paciello, Ludwigshafen am Rhein (DE); Mathias Schelwies, Ludwigshafen am Rhein (DE); Martin Haubner, Ludwigshafen am Rhein (DE); Guenter Wegner, Ludwigshafen am Rhein (DE); Gerd Tebben, Ludwigshafen am Rhein (DE); Gunnar Heydrich, Ludwigshafen am Rhein (DE); Georg Seeber, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 490 days.

(21) Appl. No.: 17/274,135

(22) PCT Filed: Sep. 3, 2019

(86) PCT No.: PCT/EP2019/073477
§ 371 (c)(1),
(2) Date: Mar. 5, 2021

(87) PCT Pub. No.: WO2020/048991
PCT Pub. Date: Mar. 12, 2020

(65) Prior Publication Data
US 2021/0371361 A1    Dec. 2, 2021

(30) Foreign Application Priority Data
Sep. 5, 2018 (EP) .................................... 18192739

(51) Int. Cl.
*C07C 29/141* (2006.01)
*B01J 10/00* (2006.01)
(Continued)

(52) U.S. Cl.
CPC ............. *C07C 29/141* (2013.01); *B01J 3/042* (2013.01); *B01J 10/00* (2013.01); *B01J 10/002* (2013.01);
(Continued)

(58) Field of Classification Search
CPC ....... C07C 29/141; B01J 3/042; B01J 19/244; B01J 10/002; B01J 4/002
See application file for complete search history.

(56) References Cited

U.S. PATENT DOCUMENTS

| 4,000,212 A | 12/1976 | Chapman |
| 6,277,333 B1 | 8/2001 | Schutte et al. |
| 2018/0057437 A1 | 3/2018 | Schelwies et al. |

FOREIGN PATENT DOCUMENTS

| DE | 19650959 A1 | 6/1998 | |
| DE | EP 1338333 A1 * | 8/2003 | .............. B01J 19/24 |

(Continued)

OTHER PUBLICATIONS

International Preliminary Report on Patentability received for PCT Patent Application No. PCT/EP2019/073477, dated Nov. 27, 2020, 21 pages (7 pages of English Translation and 14 pages of Original Document).

(Continued)

*Primary Examiner* — Yate' K Cutliff
(74) *Attorney, Agent, or Firm* — Faegre Drinker Biddle & Reath LLP

(57) ABSTRACT

A reactor for performing a gas/liquid biphasic high-pressure reaction with a foaming medium, comprising an interior (Continued)

formed by a cylindrical, vertically oriented elongate shell, a bottom and a cap, wherein the interior is divided by internals into a backmixed zone and a zone of limited backmixing, wherein the backmixed zone and the zone of limited backmixing are consecutively traversable by the reaction mixture, wherein the backmixed zone comprises means for introducing gas and liquid and a gas outlet and also comprises at least one mixing apparatus selected from a stirrer, a jet nozzle and means for injecting the gas, and the zone of limited backmixing comprises a reaction product outlet, a first cylindrical internal element which in the interior extends in the longitudinal direction of the reactor and which delimits the zone of limited backmixing from the backmixed zone, backmixing-preventing second internal elements in the form of random packings, structured packings or liquid-permeable trays arranged in the zone of limited backmixing and a riser tube whose lower end is arranged within the backmixed zone and whose upper end opens into the zone of limited backmixing so that liquid from the backmixed zone can ascend into the zone of limited backmixing via the riser tube, wherein flow into the zone of limited backmixing enters from below. The reactor is configured such that the high-pressure reaction space is optimally utilized and contamination of workup steps or subsequent reactions arranged downstream of the high-pressure reaction with foam is substantially avoided. The invention further relates to a process for performing a continuous gas/liquid biphasic high-pressure reaction in the reactor.

15 Claims, 1 Drawing Sheet

(51) Int. Cl.
*B01J 3/04* (2006.01)
*B01J 19/00* (2006.01)
*B01J 19/24* (2006.01)
*B01J 19/26* (2006.01)
*B01J 19/30* (2006.01)
*B01J 19/32* (2006.01)
*B01J 31/20* (2006.01)

(52) U.S. Cl.
CPC ......... *B01J 19/0066* (2013.01); *B01J 19/244* (2013.01); *B01J 19/2465* (2013.01); *B01J 19/26* (2013.01); *B01J 19/30* (2013.01); *B01J 19/32* (2013.01); *B01J 31/20* (2013.01); *B01J 2219/0009* (2013.01); *B01J 2219/0025* (2013.01); *B01J 2219/00092* (2013.01); *B01J 2219/00096* (2013.01); *B01J 2219/185* (2013.01); *B01J 2219/1943* (2013.01); *B01J 2531/822* (2013.01); *C07B 2200/07* (2013.01)

(56) References Cited

FOREIGN PATENT DOCUMENTS

| EP | 1338333 A1 | 8/2003 |
| WO | 2006/040096 A1 | 4/2006 |
| WO | 2008/132057 A1 | 11/2008 |

OTHER PUBLICATIONS

International Search Report and Written Opinion received for PCT Patent Application No. PCT/EP2019/073477, dated Oct. 15, 2019, 12 pages (2 pages of English Translation and 10 pages of Original Document).

* cited by examiner

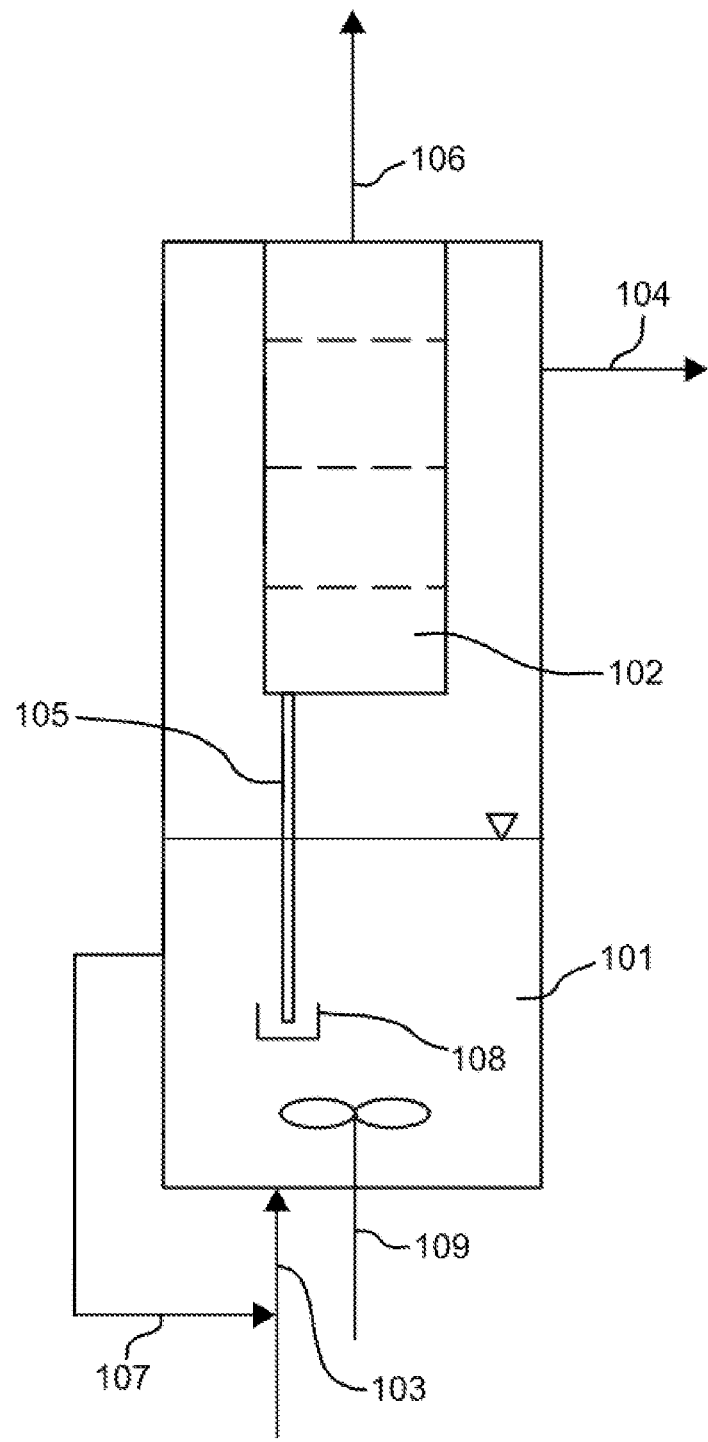

REACTOR FOR CARRYING OUT A GAS-LIQUID TWO-PHASE HIGH-PRESSURE REACTION WITH A FOAMING MEDIUM

CROSS-REFERENCE TO RELATED APPLICATIONS

This application is a national stage application (under 35 U.S.C. § 371) of PCT/EP2019/073477, filed Sep. 3, 2019, which claims benefit of European Application No. 18192739.3, filed Sep. 5, 2018, both of which are incorporated herein by reference in their entirety.

The invention relates to a reactor for performing a gas/liquid biphasic high-pressure reaction with a foaming medium. The invention further relates to a process for performing a continuous gas/liquid biphasic high-pressure reaction with a foaming medium in the reactor.

Numerous chemical and physical transformations of matter result in more or less intensive foam formation which impedes processing or makes it impossible. There is therefore a need for targeted measures for destroying the foam and/or avoiding formation thereof or at least reducing it to an acceptable level. While foam formation may sometimes be avoided or reduced through flow management in the reactors, for instance by avoiding sharp flow deflections and liquid inflow below the liquid surface, such measures are insufficient in many cases. It is therefore necessary to make use of processes for foam destruction including thermal, chemical and mechanical processes—an overview is provided by Pahl et al. in Chem.-Ing.-Tech. 67 (1995), 300-312. The known measures for foam destruction increase the technical complexity of the relevant process.

Foam may be divided into two categories. "Bubble dispersions" are foams in which the gas holdup is less than 50%. Bubble dispersion has the feature that the gas bubbles are distributed in the reactor approximately equally. Bubble dispersions occur when the medium has a high viscosity and the gas bubbles do not coalesce. Another type of foam is polyhedron foam which forms in surfactant-comprising liquids when gas is introduced. The surfactant-containing liquid forms a three-dimensional network of liquid lamellae which enclose the gas and thus form polyhedra. The polyhedron foam collects at the surface of the medium.

In the case of gas/liquid biphasic reactions an intensive commixing of the gas phase and the liquid phase is desired to achieve a high conversion; foam formation often cannot be entirely avoided. However contamination of downstream workup steps or subsequent reactions with foam or gas phase is usually undesired. In the case of high-pressure reactions foam formation also prevents optimal utilization of the high-pressure reaction space.

DE 10 2015 114 510 A1 describes a vibration apparatus for reducing foam formation in a biogas fermenter which degrades foam formed in the fermenter.

DE 196 50 959 A1 describes a process for reducing/avoiding foam formation in chemical and physical transformations of matter in which ascending jet circulation is brought about using gas injection in a reactor which narrows in the downward direction.

Asymmetric hydrogenation often employs in the reaction mixture soluble rhodium catalysts which in a form appearing in the catalyst cycle comprise a CO ligand. The catalyst is preformed, i.e. pretreated with a gas mixture comprising carbon monoxide and hydrogen, prior to the asymmetric hydrogenation. Excess carbon monoxide is separated from the thus obtained catalyst prior to its use in the asymmetric hydrogenation. In industrial practice the catalyst residue from which the hydrogenation product has been separated, for example by distillation, and which comprises the catalyst dissolved in high-boilers in its CO-deficient form is sent to preforming and subsequently returned to the hydrogenation reaction. Unfortunately the catalyst residue has a propensity for severe foaming which impedes preforming and/or subsequent separation of carbon monoxide.

It is the object of the invention to provide a reactor for performing a gas/liquid biphasic high-pressure reaction with a foaming medium which is configured such that the high-pressure reaction space is optimally utilized and contamination of workup steps or subsequent reactions arranged downstream of the high-pressure reaction with foam is substantially avoided.

The object is achieved by a reactor for performing a gas/liquid biphasic high-pressure reaction with a foaming medium comprising
an interior formed by a cylindrical, vertically oriented elongate shell, a bottom and a cap,
wherein the interior is divided by internals into a backmixed zone and a zone of limited backmixing, wherein the backmixed zone and the zone of limited backmixing are consecutively traversable by the reaction mixture, wherein the backmixed zone comprises means for introducing gas and liquid and a gas outlet and also comprises at least one mixing apparatus selected from a stirrer, a jet nozzle and means for injecting the gas, and the zone of limited backmixing comprises a reaction product outlet,
a first cylindrical internal element which in the interior extends in the longitudinal direction of the reactor and which delimits the zone of limited backmixing from the backmixed zone,
backmixing-preventing second internal elements in the form of random packings, structured packings or liquid-permeable trays arranged in the zone of limited backmixing and a riser tube whose lower end is arranged within the backmixed zone and whose upper end opens into the zone of limited backmixing so that liquid from the backmixed zone can ascend into the zone of limited backmixing via the riser tube,
wherein flow into the zone of limited backmixing enters from below.

A high-pressure reaction is to be understood as meaning a reaction performed at a pressure elevated with respect to ambient pressure, for example at at least 5 bar absolute, at least 20 bar absolute or at least 50 bar absolute.

The reactor comprises an interior formed by a cylindrical, vertically oriented elongate shell, a bottom and a cap. The ratio of the length to diameter of the shell is typically 2:1 to 100:1, preferably 5:1 to 100:1, particularly preferably 5:1 to 50:1, very particularly preferably 5:1 to 30:1.

The interior of the reactor is divided by means of internals into a backmixed zone and a zone of limited backmixing. The backmixed zone and the zone of limited backmixing are consecutively traversable by the reaction mixture. Flow into the zone of limited backmixing enters from below, preferably via a passage such as a jet nozzle at the bottom of the zone of limited backmixing. A first cylindrical internal element in the interior extends in the longitudinal direction of the reactor and delimits the zone of limited backmixing from the backmixed zone.

It is preferable when the volume ratio of the backmixed zone to the zone of limited backmixing is in the range from 0.25:1 to 4:1, particularly preferably in the range from 0.3:1 to 3:1. A reactor having a volume ratio in this range allows optimal utilization of the reactor space.

When a gas/liquid biphasic high-pressure reaction is performed in the reactor according to the invention, gas collects in the upper portion of the backmixed zone and forms a gas phase while the lower portion of the backmixed zone contains a liquid phase. Foam formed in the backmixed zone typically floats on the liquid phase.

Introduction of gas and liquid is carried out at any desired point of the backmixed zone.

The backmixed zone comprises at least one mixing apparatus selected from a stirrer, a jet nozzle and means for injecting the gas. This ensures that the gas and the liquid are brought into intensive contact with one another.

In one embodiment the mixing apparatus is a stirrer, for example a propeller stirrer.

In a preferred embodiment the introduction of gas and liquid is carried out such that this simultaneously brings about commixing of the backmixed zone. In this case the means for introducing liquid are configured as a mixing apparatus, namely as a jet nozzle, and/or the means for introducing gas are configured as a mixing apparatus, namely as means for injecting the gas.

The introduction of the liquid is preferably carried out via a jet nozzle. The introduction via a jet nozzle may be carried out above or below the separation level of the gas and the liquid, in particular via an upwardly oriented jet nozzle arranged on the bottom of the backmixed zone.

The jet nozzle can be configured as a single-fluid or two-fluid nozzle. In the case of the single-fluid nozzle only one liquid is introduced. The advantage of this configuration is the simple construction of such a single-fluid nozzle. In the case of the two-fluid nozzle the gas and the liquid are fed and dispersed together.

In order to jointly introduce the gas together with the liquid the jet nozzle may be configured as a mixing nozzle, for example a multistream ejector mixing nozzle (liquid jet ejector). The term "mixing nozzle" typically refers to a tube that narrows in the flow direction. The ejected fast jet generates negative pressure in an aspiration space surrounding the nozzle. This allows the gas to be aspirated and through impulse exchange dispersed in the liquid and jointly therewith released into the backmixed zone.

In a further embodiment the mixing apparatus comprises means for injecting the gas into the liquid. Suitable means for injecting the gas are for example a compressor for aspirating and compressing the gas above the separation level or of fresh gas and nozzles for injecting the compressed gas below the separation level.

The backmixed zone is suitably configured as an ascending jet reactor which via punctate or linear fluid injection allows large-scale recirculation of the content of the backmixed zone. In one embodiment the backmixed zone is substantially free from internals such as baffles, stirrers and the like. This allows greater flexibility when adjusting the liquid level.

The backmixed zone is preferably configured as a loop reactor. Examples of loop reactors are tubular reactors having internal and external loops. Such reactors are described in more detail for example in Ullmann's Encyclopedia (Ullmann's Encyclopedia of Industrial Chemistry, Verlag Chemie, Electronic Release 2008, 7th Edition, Chapters "Stirred Tank and Loop Reactors" and "Bubble Columns").

The loop reactor generally has an external circuit (external loops). A loop reactor having an external circuit generally has a takeoff at any desired point in the backmixed zone, preferably in the lower region of the backmixed zone, through which the reaction mixture is in an external circuit returned to the injection nozzle using a conveying apparatus. The conveying apparatus is preferably a pump and the external circuit is therefore typically referred to as a pumped circulation circuit.

Examples of pumps are centrifugal pumps or rotary piston pumps, such as rotary lobe pumps, rotary vane pumps, circumferential piston pumps or gear pumps. It is particularly preferable to employ centrifugal pumps as the conveying apparatus.

It is preferable when the external circuit of the loop reactor comprises a heat exchanger. In the context of the present invention a thus configured loop reactor is referred to as a loop reactor with external heat exchanger.

The heat exchanger is for example a tube bundle heat exchanger, double tube heat exchanger, plate heat exchanger or spiral heat exchanger. At reactor design pressures below 100 bar it is preferable to use a tube bundle heat exchanger while at higher pressures it is preferable to use one or more double tube heat exchangers connected in series.

The loop reactor with external heat exchanger is typically operated such that a portion of the reaction mixture from the backmixed zone is conveyed through the external pumped circulation circuit comprising the external heat exchanger, thus cooling the reaction mixture conveyed through the heat exchanger. The external pumped circulation generally vigorously commixes and recirculates the reaction mixture in the first reaction stage so that the residence time in the first stage typically corresponds to that of a continually backmixed stirred tank (CSTR). The reaction mixture is finally returned to the backmixed zone by means of the injection nozzle. Typically, fresh gas and fresh liquid are introduced into the pumped circulation circuit and together with the stream already present in the pumped circulation circuit supplied to the backmixed zone as reaction mixture.

The backmixed zone has a gas outlet. Unconverted gas may be withdrawn via said outlet. The gas outlet is preferably located at the upper end of the cylindrical shell. The reactor is advantageously configured such that the withdrawn unconverted gas may be at least partially reintroduced into the reaction mixture in the backmixed zone via the injection nozzle. To this end the unconverted gas from the gas outlet may be passed to the injection nozzle via an external gas conduit.

In the backmixed zone severe foaming and/or a high liquid level can result in foam ascending from the liquid phase up to the gas outlet. Contamination with foam of the gas outlet and conduits attached thereto is typically undesired. The extent of foam formation is generally variable and difficult to predict. It is generally necessary to prevent the presence of foam in the region of the gas outlet.

In one embodiment the reactor preferably comprises at least one third internal element which is arranged in the upper half of the backmixed zone and has a surface which promotes the propensity to coalescence of foaming media. Suitable internal elements which promote the propensity to coalescence of foaming media comprise elements for chemical, thermal or mechanical foam destruction. An overview is provided by Pahl et al. in Chem.-Ing.-Tech. 67 (1995), 300-312. In one embodiment the reactor comprises mechanical foam destruction measures, for example rotating elements or internals for sprinkling with autogenous liquid.

The reactor comprises a riser tube. The riser tube is arranged such that its lower end is immersed in the liquid phase during the gas/liquid biphasic high-pressure reaction. The foam generated during the reaction typically has the result that the boundary between the liquid phase and the gas phase in the backmixed zone is not clearly definable. The riser tube is suitably immersed into the liquid to such a depth that substantially no foam can penetrate into the riser tube during the reaction. Accordingly, liquid ascends from the backmixed zone into the zone of limited backmixing without entrainment of significant amounts of foam. This substantially avoids contamination of downstream workup steps or subsequent reactions with foam. This effect is particularly pronounced in the case of foams floating on the liquid phase, such as polyhedra foams.

The lower end of the riser tube is arranged at a distance from the bottom. During operation, the lower end of the riser tube has a distance from the bottom which is in the range from 10% to 95%, particularly preferably 30% to 90% and very particularly preferably 70% to 80% of the height of the liquid level.

The riser tube typically has a diameter in the range from 1% to 90%, preferably 2% to 50%, very particularly preferably 5% to 20%, of the diameter of the zone of limited backmixing.

The reactor preferably comprises a fourth internal element which is arranged at the lower end of the riser tube and which substantially prevents entry of gas bubbles into the riser tube. In particular, the shape and arrangement of the fourth internal element substantially prevent gas bubbles ascending in the reaction mixture from entering the riser tube. The fourth internal element is preferably selected from a deflection weir and a U-tube, particularly preferably is a deflection weir.

The backmixing in the zone of limited backmixing is limited by backmixing-preventing second internal elements. The installation of such apparatuses generally limits the circulation and thus the backmixing of gas and liquid. The residence time distribution in the zone of limited backmixing approximates that of a tubular reactor. This defined liquid residence time ensures that a high conversion in the high-pressure reaction is achieved.

The proportion of the gas phase in the reaction mixture in the zone of limited backmixing is preferably reduced compared to the backmixed zone. This effect may be achieved for example through the use of a riser tube and optionally a fourth internal element which substantially prevents entry of gas into the riser tube. Reducing a discrete gas phase in the zone of limited backmixing makes it possible to increase the liquid holdup in the zone of limited backmixing and increase the residence time of the liquid phase in the zone of limited backmixing. Since high-pressure reactions are carried out substantially in the liquid phase the reaction space is thus optimally utilized.

The limiting of backmixing in the zone of limited backmixing may be realized through installation of various internals. In one preferred embodiment the limiting of backmixing is effected through installation of a plurality of fixedly arranged trays in the zone of limited backmixing. This forms individual segments ("compartments") having defined reaction volumes between the individual trays. Each of the individual segments generally acts as an individual, backmixed stirred tank reactor. As the number of individual segments in series increases the residence time distribution of such a cascade generally approaches the residence time of a tubular reactor.

The number of the thus formed individual segments is preferably 2 to 20, particularly preferably 2 to 10, especially preferably 3 to 6. The volume of the individual segments formed is typically substantially identical. The trays are preferably liquid-permeable trays. It is particularly preferable when the trays are perforated plates.

In a further embodiment the limiting of backmixing is effected through installation of random packings. The random packings may have different shapes and are usually about 2 to 15 mm in size. Known examples include spherical and cylindrical solid bodies, raschig rings (a hollow cylinder), pall rings, hiflow rings, Intalox saddles and the like. The random packings are preferably solid bodies. The random packings may be introduced into the zone of limited backmixing in ordered or disordered form (as a dumped bed). Materials that may be employed include glass, ceramic, metal and plastics.

In a further embodiment the limiting of backmixing is effected through incorporation of structured packings. Structured packings are a further development of ordered random packings. They have a regular structure. There are various designs of packings, such as woven or sheet metal packings. Materials that may be employed include metal, plastic, glass and ceramic.

The first internal element is preferably arranged concentrically to the shell so that the zone of limited backmixing has a circular horizontal cross section. The ratio of length to diameter of the zone of limited backmixing is typically 2:1 to 100:1, preferably 5:1 to 50:1, particularly preferably 7:1 to 25:1.

Also provided is a process for performing a continuous gas/liquid biphasic high-pressure reaction in which in a reactor according to any of the preceding claims a gas and a liquid are introduced into the backmixed zone, liquid is allowed to ascend from the backmixed zone into the zone of limited backmixing through the riser tube, unconverted gas is at least partially discharged via the gas outlet and a reaction product is withdrawn at the reaction product outlet.

It is advantageous when the unconverted gas is at least partially reintroduced via the injection nozzle into the reaction mixture in the backmixed zone, for example via an external gas conduit.

The backmixed zone is suitably at a higher pressure than the reaction product outlet in order to overcome the hydrostatic pressure in the zone of limited backmixing and the pressure drop generated upon traversal of the backmixing-preventing second internal elements. The higher pressure in the backmixed zone causes liquid to ascend from the backmixed zone into the zone of limited backmixing. The first cylindrical internal element and the backmixing-preventing second internal elements must be configured according to this differential pressure.

In one embodiment the process is a process for preforming a homogeneous rhodium hydrogenation catalyst comprising at least one CO ligand. A process for treating a CO-deficient rhodium hydrogenation catalyst with a gas mixture comprising carbon monoxide and hydrogen is thus concerned. The liquid comprises a dissolved CO-deficient rhodium hydrogenation catalyst and the gas comprises hydrogen and carbon monoxide, wherein the reaction of the CO-deficient rhodium hydrogenation catalyst with the gas affords a hydrogenation-active rhodium hydrogenation catalyst.

The reaction product of the preforming which comprises the hydrogenation-active rhodium hydrogenation catalyst may then be supplied to an asymmetric hydrogenation reaction together with a substrate to be hydrogenated to afford a hydrogenation reaction mixture. After separation of the hydrogenation product the residue comprising CO-deficient rhodium hydrogenation catalyst is returned to the preforming. The hydrogenation product may be separated from the hydrogenation mixture by processes known per se to those skilled in the art, for example by distillation and/or flash evaporation, wherein the hydrogenation-active rhodium hydrogenation catalyst loses CO and a CO-deficient rhodium hydrogenation catalyst remains.

In one embodiment the substrate to be hydrogenated is cis-citral. The hydrogenation product of cis-citral is R-citronellal.

The rhodium catalysts used for hydrogenation comprise at least one CO ligand at least in a form appearing in the catalyst cycle or in a precursor form preceding the actual catalyst cycle, it being immaterial whether this catalyst form comprising at least one CO ligand constitutes the actual catalytically active catalyst form. In order to stabilize the catalyst forms comprising CO ligands it may be advantageous to additionally supply carbon monoxide to the reaction mixture during the hydrogenation.

The rhodium catalyst typically comprises at least one optically active ligand. Such catalysts are obtainable for example by reaction of a suitable rhodium compound soluble in the hydrogenation mixture and having an optically active ligand comprising at least one phosphorus and/or arsenic atom.

Examples of employable rhodium compounds are: $RhCl_3$, $Rh(OAc)_3$, $[Rh(cod)Cl]_2$, $Rh(CO)_2acac$, $[Rh(cod)OH]_2$, $[Rh(cod)OMe]_2$, $Rh_4(CO)_{12}$, $Rh_6(CO)_{16}$, wherein "acac" stands for an acetylacetonate ligand and "cod" stands for a cyclooctadiene ligand.

The recited rhodium compounds are contacted with a further compound which is optically active, preferably substantially enantiomerically pure (i.e. having an enantiomeric excess of at least about 99%), and comprises at least one phosphorus and/or arsenic atom, preferably at least one phosphorus atom. This compound to be described as a chiral ligand forms the rhodium catalyst with the employed rhodium compound.

Such chiral ligands which comprise two phosphorus atoms and form chelate complexes with rhodium are especially preferred.

Chiral ligands suitable in the context of the present invention include compounds such as are described for example in: I. Ojima (ed.), Catalytic Asymmetric Synthesis, Wiley-VCh, 2nd edition, 2000 or in E. N. Jacobsen, A. Pfaltz, H. Yamamoto (ed.), Comprehensive Asymmetric Catalysis, 2000, Springer or in W. Tang, X. Zhang, Chem. Rev. 2003, 103, 3029-3069.

Preferred ligands are chiral bidentate bisphosphine ligands, especially those of general formulae (I) to (Ill)

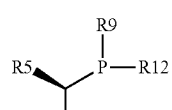

(I)

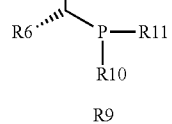

(II)

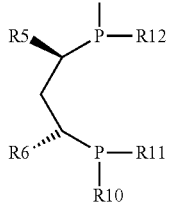

(III)

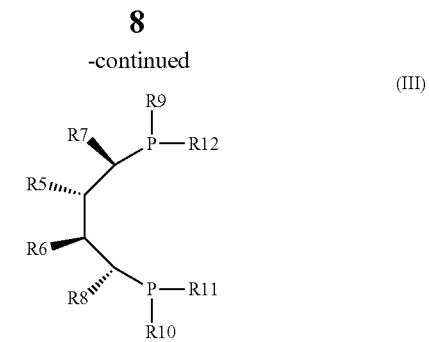

wherein
$R^5$, $R^6$ each independently of one another represent an unbranched, branched or cyclic hydrocarbon radical having 1 to 20 carbon atoms which is saturated or may comprise one or more, generally 1 to about 4, nonconjugated ethylenic double bonds and which is unsubstituted or bears one or more, generally 1 to 4, identical or different substituents selected from $OR^{13}$, $NR^{14}R^{15}$, halogen, $C_6$-$C_{10}$-aryl and $C_3$-$C_9$-hetaryl, or
$R^5$ and $R^6$ may jointly represent a 2- to 10-membered alkylene group or a 3- to 10-membered cycloalkylene group, wherein 1, 2, 3 or 4 nonadjacent CH groups may be replaced by O or N—$R^{13}$, wherein the alkylene group and the cycloalkylene group are saturated or comprise one or two nonconjugated ethylenic double bonds and wherein the alkylene group and the cycloalkylene group are unsubstituted or bear one or more identical or different substituents selected from $C_1$-$C_4$-alkyl;
$R^7$, $R^8$ each independently of one another represent hydrogen or straight-chain or branched $C_1$-$C_4$-alkyl and
$R^9$, $R^{10}$, $R^{11}$, $R^{12}$ are identical or different and represent $C_6$-$C_{10}$-aryl which is unsubstituted or bears one or more substituents selected from $C_1$-$C_6$-alkyl, $C_3$-$C_6$-cycloalkyl, $C_6$-$C_{10}$-aryl, $C_1$-$C_6$-alkoxy and amino;
$R^{13}$, $R^{14}$, $R^{15}$ each independently of one another represent hydrogen, $C_1$-$C_4$-alkyl, $C_6$-$C_{10}$-aryl, $C_7$-$C_{12}$-aralkyl or $C_7$-$C_{12}$-alkylaryl, wherein $R^{14}$ and $R^{15}$ may also jointly represent an alkylene chain having 2 to 5 carbon atoms which may be interrupted by N or O.

Having regard to the formulae (I), (II) and (III) the variables are especially as follows:
$R^5$, $R^6$ each independently of one another represent $C_1$-$C_4$-alkyl or
$R^5$ and $R^6$ jointly represent a $C_3$-$C_5$-alkanediyl radical $C_3$-$C_7$-alkenediyl radical, $C_5$-$C_7$-cycloalkanediyl radical or a $C_5$-$C_7$-cycloalkenediyl radical, wherein the four abovementioned radicals are unsubstituted or bear one or more identical or different substituents selected from $C_1$-$C_4$-alkyl;
$R^7$, $R^8$ each independently of one another represent hydrogen or $C_1$-$C_4$-alkyl;
$R^9$, $R^{10}$, $R^{11}$, $R^{12}$ each represent phenyl.

Chiral, bidentate bisphosphine ligands particularly preferred on account of being readily available are compounds obtainable under the designation "chiraphos" and having the formula:

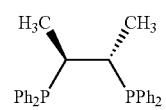

The chiral ligands are advantageously employed in an amount of about 0.9 to about 10 mol, preferably about 1 to about 4 mol, per mol of employed rhodium compound. The optically active rhodium catalyst is suitably generated in situ by reaction of an achiral rhodium compound with a chiral, bidentate bisphosphine ligand. In this context the term "in situ" is to be understood as meaning that the catalyst is generated immediately before hydrogenation.

It has been found that the presence of monodentate ligands can increase the activity of the catalyst. In a preferred embodiment of the process according to the invention compounds of formula (IV)

are employed, for example in the liquid introduced into the reactor, wherein Z in formula (IV) represents a $CHR^{18}R^{19}$ group and wherein the variables $R^{16}$, $R^{17}$, $R^{18}$, $R^{19}$ independently of one another and especially jointly are as follows:

$R^{16}$, $R^{17}$: are identical or different and represent phenyl which is unsubstituted or bears 1, 2 or 3 substituents selected from methyl and methoxy, wherein $R^{16}$ and $R^{17}$ each especially represent unsubstituted phenyl;

$R^{18}$ represents $C_1$- to $C_4$-alkyl, especially methyl;

$R^{19}$ represents $C_1$- to $C_4$-alkyl bearing a $P(=O)R^{19a}R^{19b}$ group and especially a $CH_2-P(=O)R^{19a}R^{19b}$ or $CH(CH_3)-P(=O)R^{19a}R^{19b}$ group;

wherein $R^{19a}$, $R^{19b}$: are identical or different and represent phenyl which is unsubstituted or bears 1, 2 or 3 substituents selected from methyl and methoxy, wherein particularly preferably $R^{19a}$ and $R^{19b}$ each represent unsubstituted phenyl.

In this preferred embodiment of the process according to the invention it is particularly preferable to employ a compound of formula (IV), wherein $R^{16}$, $R^{17}$: represent unsubstituted phenyl;

$R^{18}$ represents methyl;

$R^{19}$ represents a $CH(CH_3)-P(=O)R^{19a}R^{19b}$ group, wherein $R^{19a}$ and $R^{19b}$ each represent unsubstituted phenyl.

This is the compound (2-(diphenylphosphoryl)-1-methylpropyl)diphenylphosphane (chiraphos monooxide) including the (R,R) enantiomer (=(R,R)-chiraphos monooxide) and the (S,S) enantiomer (=(S,S)-chiraphos monooxide) and mixtures of (R,R)-chiraphos monooxide and (S,S)-chiraphos monooxide.

When the radicals $R^{18}$ and $R^{19}$ in general formula (IV) are different the carbon atom bearing the radicals $R^{18}$ and $R^{19}$ may have an (R) or (S) configuration. These compounds of general formula (IV) may be in the form of pure (R) or pure (S) stereoisomers or as mixtures thereof. Generally employed in these cases are the pure (R) and (S) stereoisomers, wherein any stereoisomer mixtures are also suitable for use in the present process.

A pure stereoisomer is here and hereinbelow to be understood as meaning chiral substances which in terms of the desired stereoisomer have an enantiomeric excess (ee) of at least 80% ee, in particular at least 90% ee and especially 95% ee.

In particular, the chiral ligand employed is chiraphos and the monodentate compound employed is (2-(diphenylphosphoryl)-1-methylpropyl)diphenylphosphane (chiraphos monooxide). By way of example the chiral ligand employed is R-chiraphos and the monodentate compound employed is (R,R)-chiraphos monooxide and/or (S,S)-chiraphos monooxide. As an alternative, the chiral ligand employed is S-chiraphos and the monodentate compound employed is (R,R)-chiraphos monooxide and/or (S,S)-chiraphos monooxide.

According to the invention the compound of formula (IV) is generally employed in an amount of 0.01 to 1 mol, preferably 0.02 to 0.8 mol, particularly preferably 0.03 to 0.7 mol and especially in an amount of 0.04 to 0.6 mol per mol.

Further embodiments of the hydrogenation catalyst and of the monodentate ligand are described in US 2018/0057437 A1, WO 2006/040096 A1 and WO 2008/132057 A1.

Preforming the rhodium catalyst typically comprises dissolving the selected rhodium compound and the selected chiral ligand in a suitable solvent/dissolution medium inert under the reaction conditions such as for example ether, tetrahydrofuran, methyltetrahydrofuran, toluene, xylenes, chlorobenzene, octadecanol, biphenyl ether, Texanol, Marlotherm, Oxo Oil 9N (hydroformylation products of isomeric octenes, BASF Aktiengesellschaft), citronellal and the like. Employable dissolution media may also include the hydrogenation product or any high-boiling byproducts generated during the conversion. In the reactor according to the invention the resulting solution is pressurized with a gas mixture comprising hydrogen and carbon monoxide at a pressure of typically about 5 to about 350 bar, preferably of about 20 to about 200 bar and particularly preferably of about 50 to about 100 bar. Preforming preferably employs a gas mixture comprising about 30 to 99 vol % of hydrogen,
1 to 70 vol % of carbon monoxide and
0 to 5 vol % of further gases, wherein the reported amounts in vol % sum to 100 vol %.

A gas mixture especially preferred for preforming is so-called synthesis gas which typically comprises about 35 to 55 vol % of carbon monoxide in addition to hydrogen and traces of further gases.

The preforming of the catalyst is typically performed at temperatures of about 25° C. to about 100° C., preferably at about 40° C. to about 80° C. The preforming is typically completed after about 1 h to about 24 h, often after about 1 to about 12 h. Preforming is preferably followed by asymmetric hydrogenation of a selected substrate. After the preceding preforming the selected substrate may generally be successfully converted with or without supplying additional carbon monoxide. It is advantageous when a preforming is performed as described and additional carbon monoxide is added to the reaction mixture during the asymmetric hydrogenation.

In this embodiment the recited preforming of the catalyst precursor stage is performed at a pressure of 5 to 100 bar with a gas mixture comprising 20 to 90 vol % of carbon monoxide, 10 to 80 vol % of hydrogen and 0 to 5 vol % of further gases, wherein the recited volume fractions sum to 100 vol %. In addition, excess carbon monoxide is separated from the thus obtained catalyst before use in the asymmetric hydrogenation. The term excess carbon monoxide is to be understood as meaning carbon monoxide present in the obtained reaction mixture in gaseous or dissolved form and not bonded to the rhodium catalyst/its precursor. The excess carbon monoxide not bonded to the catalyst is thus at least largely removed, i.e. to an extent such that any residual amounts of dissolved carbon monoxide do not have a disruptive effect in the subsequent hydrogenation. This is typically ensured when about 90%, preferably about 95% or more, of the carbon monoxide employed for preforming is separated. The excess carbon monoxide is preferably completely removed from the catalyst obtained by preforming.

The separation of the excess carbon monoxide from the obtained catalyst/from the reaction mixture comprising the catalyst may be effected in various ways. The catalyst/the mixture comprising the catalyst obtained by preforming is preferably decompressed to a pressure of up to about 5 bar (absolute), preferably, especially when performing the preforming in the pressure range from 5 to 10 bar, to a pressure of less than 5 bar (absolute), preferably to a pressure in the range from about 1 bar to about 5 bar, preferably 1 to less than 5 bar, particularly preferably to a pressure in the range from 1 to 3 bar, very particularly preferably to a pressure in the range from about 1 to about 2 bar, especially preferably to standard pressure, so that gaseous, unbonded carbon monoxide escapes from the product of the preforming. The abovementioned decompression of the preformed catalyst may be carried out for example using a high-pressure separator such as is known per se to a person skilled in the art. Such separators in which the liquid is in the continuous phase are described for example in: Perry's Chemical Engineers' Handbook, 1997, 7th ed., McGraw-Hill, pp. 14.95 and 14.96; prevention of possible droplet entrainment is described on pages 14.87 to 14.90. Decompression of the preformed catalyst may be carried out in one or two stages until achievement of the desired pressure in the range from 1 bar to about 5 bar, wherein the temperature typically falls to 10° C. to 40° C. Separation of excess carbon monoxide may alternatively be achieved by so-called stripping of the catalyst/the mixture comprising the catalyst with a gas, advantageously with a gas inert under the reaction conditions. The term stripping is understood by those skilled in the art to mean introduction of a gas into the catalyst/the reaction mixture comprising the catalyst such as is described for example in W. R. A. Vauck, H. A. Müller, Grundoperationen chemischer Verfahrenstechnik, Deutscher Verlag für Grundstoffchemie Leipzig, Stuttgart, 10th edition, 1984, page 800. Examples of inert gases suitable therefor include: Hydrogen, helium, neon, argon, xenon, nitrogen and/or CO2, preferably hydrogen, nitrogen, argon.

If carbon monoxide is supplied to the reaction system the supplying may be undertaken in various ways: Thus for example the carbon monoxide may be admixed with the hydrogen used for asymmetric hydrogenation or else directly introduced into the reaction solution in gaseous form. The carbon monoxide is preferably admixed with the hydrogen used for asymmetric hydrogenation.

The asymmetric hydrogenation is preferably performed with hydrogen having a carbon monoxide content in the range from 50 to 3000 ppm, in particular in the range from 100 to 2000 ppm, especially in the range from 200 to 1000 ppm and very especially in the range from 400 to 800 ppm.

The hydrogenation product may be separated from the hydrogenation mixture by processes known per se to those skilled in the art such as for example by distillation and/or flash evaporation and the remaining catalyst utilized in the context of further conversions. In the context of the preferred embodiment it is advantageous to eschew addition of solvents and perform the recited conversions in the substrate to be converted/the product and optionally in high-boiling byproducts as the dissolution medium. Especial preference is given to the continuous reaction mode with reuse/recycling of the homogeneous catalyst stabilized according to the invention.

In a preferred embodiment a prochiral α,β-unsaturated carbonyl compound is hydrogenated. A prochiral α,β-unsaturated carbonyl compound can form a chirality center by addition reaction at the olefinic double bond. To this end the double bond bears four different substituents. The prochiral α,β-unsaturated carbonyl compound is preferably selected from compounds of general formula (V)

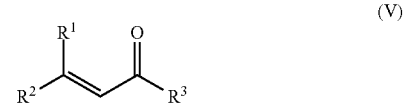

wherein
$R^1$, $R^2$ are distinct from one another and each represent an unbranched, branched or cyclic hydrocarbon radical having 1 to 25 carbon atoms which is saturated or comprises one or more, nonconjugated ethylenic double bonds and which is unsubstituted or bears one or more identical or different substituents selected from $OR^4$, $NR^{5a}R^{5b}$, halogen, $C_6$-$C_{10}$-aryl and hetaryl having 5 to 10 ring atoms,
$R^3$ represents hydrogen or an unbranched, branched or cyclic hydrocarbon radical having 1 to 25 carbon atoms which is saturated or comprises one or more, nonconjugated ethylenic double bonds and which is unsubstituted or bears one or more identical or different substituents selected from $OR^4$, $NR^{5a}R^{5b}$, halogen, $C_6$-$C_{10}$-aryl and hetaryl having 5 to 10 ring atoms,
or
$R^3$ jointly with either of the radicals $R^1$ or $R^2$ may also represent a 3- to 25-membered alkylene group wherein 1, 2, 3 or 4 nonadjacent $CH_2$-groups may be replaced by O or N—$R^{5c}$, wherein the alkylene group is saturated or comprises one or more nonconjugated ethylenic double bonds and wherein the alkylene group is unsubstituted or bears one or more identical or different substituents selected from $OR^4$, $NR^{5a}R^{5b}$, halogen, $C_1$-$C_4$-alkyl, $C_6$-$C_{10}$-aryl and hetaryl having 5 to 10 ring atoms, wherein two substituents may also jointly represent a 2- to 10-membered alkylene group, wherein the 2- to 10-membered alkylene group is saturated or comprises one or more nonconjugated ethylenic double bonds and wherein the 2- to 10-membered alkylene group is unsubstituted or bears one or more identical or different substituents selected from $OR^4$, $NR^{5a}R^{5b}$, halogen, $C_6$-$C_{10}$-aryl and hetaryl having 5 to 10 ring atoms;
wherein
$R^4$ represents hydrogen, $C_1$-$C_6$-alkyl, $C_6$-$C_{10}$-aryl, $C_6$-$C_{14}$-aryl-$C_1$-$C_{10}$-alkyl, or $C_1$-$C_{10}$-alkyl-$C_6$-$C_{14}$-aryl;
$R^{5a}$, $R^{5b}$ each independently of one another represent hydrogen, $C_1$-$C_6$-alkyl, $C_6$-$C_{10}$-aryl, $C_6$-$C_{14}$-aryl-$C_1$-$C_{10}$-alkyl or $C_1$-$C_{10}$-alkyl-$C_6$-$C_{14}$-aryl or
$R^{5a}$ and $R^{5b}$ may also jointly represent an alkylene chain having 2 to 5 carbon atoms which may be interrupted by N or O; and
$R^{5c}$ represents hydrogen, $C_1$-$C_6$-alkyl, $C_6$-$C_{10}$-aryl, $C_6$-$C_{14}$-aryl-$C_1$-$C_{10}$-alkyl, or $C_1$-$C_{10}$-alkyl-$C_6$-$C_{14}$-aryl;
In preferred embodiments the prochiral α,β-unsaturated carbonyl compound is selected from compounds of general formulae (Va) and (Vb)

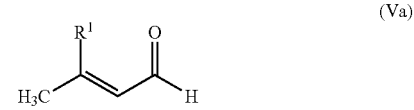

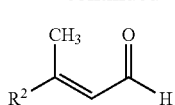

wherein
R¹, R² each represent an unbranched or branched hydrocarbon radical having 2 to 25 carbon atoms which is saturated or comprises 1, 2, 3, 4 or 5 nonconjugated ethylenic double bonds.

A particularly preferred embodiment relates to a process for producing optically active citronellal of formula (VI)

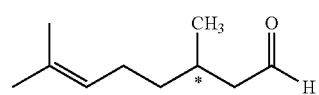

wherein * denotes the asymmetric center;
by asymmetric hydrogenation of geranial of formula (Va-1) or of neral of formula (Vb-1)

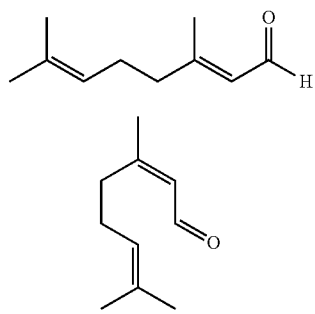

or a mixture comprising neral and geranial. A mixture comprising neral and geranial is known as citral.

The thus obtainable optically active citronellal of formula (VI) may be subjected to a cyclization to afford optically active isopulegol and the optically active isopulegol hydrogenated to afford optically active menthol.

The invention is elucidated in more detail by the accompanying FIGURE.

FIG. 1

FIG. 1 is a schematic diagram of a reactor according to the invention.

The reactor comprises a backmixed zone 101 and a zone of limited backmixing 102 whose backmixing is limited by internal trays. An injection nozzle (not shown) is used to supply a gas and a liquid from the conduit 103 to the backmixed zone 101.

The backmixed zone 101 has a gas outlet 104 through which unconverted gas is discharged. Liquid ascends from the backmixed zone 101 into the zone of limited backmixing 102 via the riser tube 105 whose lower end is arranged below the liquid level. Reaction product is discharged via the reaction product outlet 106.

The backmixed zone is in the form of a loop reactor having an external circuit 107. Arranged in the lower region of the backmixed zone is a takeoff through which the reaction mixture is returned into conduit 103 and thus to the backmixed zone 101 via the external circuit 107 using a pump (not shown).

The reactor comprises a deflection weir 108 which substantially prevents entry of gas into the riser tube 105.

The backmixed zone 101 may comprise a stirrer 109 instead of the external circuit 107.

The invention claimed is:

1. A reactor for performing a gas/liquid biphasic high-pressure reaction with a foaming medium, comprising:
   an interior formed by a cylindrical, vertically oriented elongate shell, a bottom and a cap, wherein the interior is divided by internals into a backmixed zone and a zone of limited backmixing, wherein the backmixed zone and the zone of limited backmixing are consecutively traversable by the reaction mixture, wherein the backmixed zone comprises means for introducing gas and liquid and a gas outlet and also comprises at least one mixing apparatus selected from a stirrer, a jet nozzle and means for injecting the gas, and the zone of limited backmixing comprises a reaction product outlet;
   a first cylindrical internal element which in the interior extends in the longitudinal direction of the reactor and which delimits the zone of limited backmixing from the backmixed zone;
   backmixing-preventing second internal elements in the form of random packings, structured packings or liquid-permeable trays arranged in the zone of limited backmixing;
   a riser tube whose lower end is arranged within the backmixed zone and whose upper end opens into the zone of limited backmixing so that liquid from the backmixed zone can ascend into the zone of limited backmixing via the riser tube; and
   an internal element which is arranged at the lower end of the riser tube and which prevents entry of gas into the riser tube, which internal element is selected from a deflection weir and a U-tube,
   wherein flow into the zone of limited backmixing enters from below.

2. The reactor according to claim 1, wherein the volume ratio of the backmixed zone to the zone of limited backmixing is in the range from 0.25:1 to 4:1.

3. The reactor according to claim 1, comprising at least one third internal element which is arranged in the upper half of the backmixed zone and has a surface which promotes the propensity to coalescence of foaming media.

4. The reactor according to claim 1, wherein the first internal element is arranged concentrically to the shell so that the zone of limited backmixing has a circular horizontal cross section.

5. A process for performing a continuous gas/liquid biphasic high-pressure reaction in which in a reactor according to claim 1 a gas and a liquid are introduced into the backmixed zone, said liquid is allowed to ascend from the backmixed zone into the zone of limited backmixing through the riser tube, unconverted gas is at least partially discharged via the gas outlet and a reaction product is withdrawn at the reaction product outlet.

6. The process according to claim 5 for preforming a homogeneous rhodium hydrogenation catalyst comprising at least one CO ligand, wherein the liquid comprises a dissolved CO-deficient rhodium hydrogenation catalyst and wherein the gas comprises hydrogen and carbon monoxide, wherein the reaction of the CO-deficient rhodium hydrogenation catalyst with the gas affords a hydrogenation-active rhodium hydrogenation catalyst.

7. The process according to claim 6, wherein the CO-deficient rhodium hydrogenation catalyst comprises at least one chiral ligand.

8. The process according to claim 6, wherein the liquid comprises a compound of formula (IV)

(IV)

wherein Z in formula (IV) represents a $CHR^3R^4$ group and wherein the variables $R_1$, $R_2$, $R_3$, $R^4$ independently of one another and especially jointly are as follows:
- $R^1$, $R^2$: are identical or different and represent phenyl which is unsubstituted or bears 1, 2 or 3 substituents selected from methyl and methoxy;
- $R^3$ represents $C_1$- to $C_4$-alkyl;
- $R^4$ represents $C_1$- to $C_4$-alkyl bearing a $P(=O)R^{4a}R^{4b}$ group;

wherein
- $R_{4a}$, $R_{4b}$: are identical or different and represent phenyl which is unsubstituted or bears 1, 2 or 3 substituents selected from methyl and methoxy.

9. The process according to claim 6, wherein the reaction product of the preforming is supplied to an asymmetric hydrogenation reaction together with a substrate to be hydrogenated to afford a hydrogenation reaction mixture and a hydrogenation product is separated from the hydrogenation reaction mixture to afford a residue comprising CO-deficient rhodium hydrogenation catalyst which is supplied to the preforming.

10. A process for producing optically active menthol in which optically active citronellal of formula (VI)

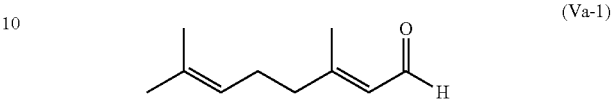

wherein * denotes the asymmetric center;

is produced by the process according to claim 9, wherein the hydrogenation reaction comprises the asymmetric hydrogenation of geranial of formula (Va-1) or of neral of formula (Vb-1)

(Va-1)

(Vb-1)

or a mixture comprising neral and geranial, the optically active citronellal of formula (VI) is subjected to a cyclization to afford optically active isopulegol and the optically active isopulegol is hydrogenated to afford optically active menthol.

11. The process of claim 6, wherein the chiral ligand is chiraphos.

12. The process of claim 8, wherein $R^1$ and $R^2$ each represent unsubstituted phenyl.

13. The process of claim 8, wherein $R^4$ represents a $CH_2$-$P(=O)R^{4a}R^{4b}$ or $CH(CH_3)$-$P(=O)R_{4a}R^{4b}$ group.

14. The process of claim 8, wherein $R^{4a}$ and $R^{4b}$ each represent unsubstituted phenyl.

15. The process of claim 8, wherein $R^3$ is methyl.

* * * * *